(12) United States Patent
Koch et al.

(10) Patent No.: US 6,914,164 B2
(45) Date of Patent: Jul. 5, 2005

(54) METHOD FOR THE DECOMPOSITION OF AMMONIUM FORMATES IN REACTION MIXTURES CONTAINING POLYOL

(75) Inventors: Michael Koch, Speyer (DE); Alexander Wartini, Heidelberg (DE); Tilman Sirch, Schifferstadt (DE); Matthias Dernbach, Dossenheim (DE)

(73) Assignee: BASF AG, Ludwigshafen (DE)

( * ) Notice: Subject to any disclaimer, the term of this patent is extended or adjusted under 35 U.S.C. 154(b) by 0 days.

(21) Appl. No.: 10/493,497

(22) PCT Filed: Oct. 18, 2002

(86) PCT No.: PCT/EP02/11671

§ 371 (c)(1),
(2), (4) Date: Apr. 22, 2004

(87) PCT Pub. No.: WO03/035594

PCT Pub. Date: May 1, 2003

(65) Prior Publication Data

US 2004/0254408 A1 Dec. 16, 2004

(30) Foreign Application Priority Data

Oct. 24, 2001 (DE) .......................................... 101 52 525

(51) Int. Cl.[7] .............................................. C07C 27/26
(52) U.S. Cl. ..................................................... 568/854
(58) Field of Search ......................................... 568/854

(56) References Cited

U.S. PATENT DOCUMENTS

| 4,122,290 | A | 10/1978 | Immel et al. |
| 4,247,485 | A | 1/1981 | Immel et al. |
| 4,386,018 | A | 5/1983 | Merger et al. |
| 4,594,461 | A | 6/1986 | Merger et al. |
| 5,149,861 | A | 9/1992 | Merger et al. |
| 5,736,484 | A | 4/1998 | Polanek et al. |
| 6,034,285 | A | 3/2000 | Doi et al. |
| 6,187,971 | B1 | 2/2001 | Kratz et al. |
| 6,448,457 | B1 | 9/2002 | Hesse et al. |
| 6,586,642 | B2 * | 7/2003 | Dernbach et al. ........... 568/854 |

FOREIGN PATENT DOCUMENTS

| DE | 25 07461 | 9/1976 | |
| DE | 27 02582 | 7/1978 | |
| DE | 28 13 201 | 10/1979 | |
| DE | 33 40 791 | 5/1985 | |
| DE | 198 48569 | 4/1999 | |
| DE | 198 09418 | 9/1999 | |
| DE | 198 26396 | 12/1999 | |
| DE | 19963442 A1 * | 7/2001 | ........... C07B/61/00 |
| EP | 44 444 | 1/1982 | |
| EP | 289 921 | 11/1988 | |
| EP | 672 452 | 9/1995 | |
| GB | 1535826 | 12/1978 | |
| WO | 98/28253 | 7/1998 | |

* cited by examiner

Primary Examiner—Michael L. Shippen
(74) Attorney, Agent, or Firm—Novak Druce & Quigg, LLP

(57) ABSTRACT

A method for removing trialkyl ammonium formate from a methylol alkanes obtained by condensation of formaldehyde with a higher aldehyde. The invention is characterized in that trialkyl ammonium formate is decomposed at a high temperature using catalysts containing at least one metal from groups 8–12 of the classification of elements in the presence of gas containing hydrogen. The method makes it possible to separate trialkyl ammonium formate according to the organic Cannizzaro method and according to the hydrogenation method.

12 Claims, No Drawings

METHOD FOR THE DECOMPOSITION OF AMMONIUM FORMATES IN REACTION MIXTURES CONTAINING POLYOL

The invention relates to the field of industrial organic chemistry. More precisely, the present invention provides a process for the effective decomposition of trialkylammonium formate which is present in methylolalkanes and has been formed from the trialkylamine used as catalyst in the preparation of the methylolalkanal and the formic acid formed as by-product.

The condensation of formaldehyde with CH-acid higher alkanals to form methylolalkanals, in general dimethylolalkanals and trimethylolalkanals, and conversion of the compounds obtained into polyols is a widely employed process in industrial chemistry. Examples of important triols obtained in this way are trimethylolpropane, trimethylolethane and trimethylolbutane, which have found widespread use in the production of surface coatings, urethanes and polyesters. Further important compounds are pentaerythritol, obtainable by condensation of formaldehyde and acetaldehyde, and also neopentyl glycol from isobutyraladehyde and formaldehyde. The tetravalent alcohol pentaerythritol is likewise frequently used in the surface coatings industry, but has also achieved great importance in the production of explosives.

The polyols mentioned can be prepared by various methods. One method is the Cannizzaro process which is further subdivided into the inorganic Cannizzaro process and the organic Cannizzaro process. In the inorganic variant, an excess of formaldehyde is reacted with the corresponding alkanal in the presence of stoichiometric amounts of an inorganic base such as NaOH or $Ca(OH)_2$. The methylolalkanal formed in the first step reacts in the second step with the excess formaldehyde in a disproportionation reaction to form the corresponding polyol and the formate of the respective base, i.e., for example, sodium or calcium formate.

In the organic Cannizzaro process, a tertiary amine, generally a trialkylamine, is used in place of the inorganic base. The reaction proceeds as described above, with one equivalent of the ammonium formate of the corresponding amine being formed. This can be worked up further by appropriate methods, so that at least the amine can be recovered and return to the reaction. The crude polyol obtained can be worked up in various ways to give the pure polyol.

A further development is the hydrogenation process in which an appropriate alkanal and formaldehyde are reacted with one another not in the presence of at least stoichiometric amounts but of catalytic amounts of a tertiary amine, generally from about 5 to 10 mol %. In this process, the reaction stops at the stage of 2,2-dimethylolalkanal which is subsequently converted into trimethylolalkane by hydrogenation. A description of the effective process may be found in WO 98/28253 of the present applicant.

A number of variants of this hydrogenation process are described, inter alia, in the patent applications DE-A-25 07 461, DE-A-27 02 582, DE-A-28 13 201 and DE-A-33 40 791.

Although the hydrogenation process advantageously does not form stoichiometric amounts of the formate as in the organic Cannizzaro process, trialkylammonium formate is formed as product of a cross-Cannizzaro reaction occurring to a small extent as secondary reaction.

Trialkylammonium formates react under particular conditions, for example, the dewatering or heating of trimethylolalkane solutions obtained, to form trialkylamine and trimethylolpropane formate. These decrease the yield of trimethylolalkane and are difficult to dissociate without undesirable degradation reactions. There is therefore particular interest in the removal of trialkylammonium formates.

DE 198 48 569 discloses a process for the decomposition of formates of tertiary amines which are present as by-products in trimethylolalkane solutions prepared by the organic Cannizzaro process. These formates are decomposed by heating, preferably in the presence of modified noble metal catalysts and under superatmospheric pressure, into hydrogen and carbon dioxide and/or water and carbon monoxide and the tertiary amine. The formate conversions in this process are unsatisfactory, and the formation of further by-products is also observed.

In addition, the abovementioned process has only limited suitability for the effective work-up of a trimethylolalkane mixture obtained by the hydrogenation process in which only catalytic amounts of trialkylamine are used and the product mixture thus also contains only small amounts of trialkyammonium formate.

It is an object of the present invention to provide a process which is suitable for the work-up of reaction mixtures obtained by the hydrogenation process and also those obtained by the organic Cannizzaro process. Furthermore, this process should make it possible to prepare trimethylolalkanes having a high purity and a low color number, preferably less than 10 Apha.

We have found that this object is achieved by a process for removing trialkylammonium formate from methylolalkanes which have been obtained by condensation of formaldehyde with a higher aldehyde, which process comprises decomposing trialkylammonium formate at elevated temperature in the presence of a hydrogen-containing gas over catalysts comprising at least one metal of groups 8 to 12 of the Periodic Table.

Methylolalkanes which can be worked up by the process of the present invention are, for example, neopentyl glycol, pentaerythritol, trimethylolpropane, trimethylolbutane, trimethylolethane, 2-ethyl-1,3-propanediol, 2-methyl-1,3-propane-diol, glycerol, dimethylolpropane, dipentaerythritol and 1,1-,1, 2-, 1,3- and 1,4-cyclohexanedimethanol.

In the process of the present invention, preference is given to removing trialkylammonium formates from trimethylolalkanes which have been prepared by the organic Cannizzaro process or the hydrogenation process. Preference is given to purifying trimethylolalkanes, particularly preferably trimethylolpropane, hereinafter referred to as TMP for short, prepared by the hydrogenation process.

The preparation of crude TMP containing trialkylammonium formate by the Cannizzaro process is disclosed, for example, in DE 198 48 569.

In the hydrogenation process, the TMP is obtained by condensation of n-butyraldehyde with formaldehyde in the presence of catalytic amounts of a tertiary amine and subsequent catalytic hydrogenation of the dimethylolbutanal mixture formed. This crude TMP does not contain any alkali metal or alkaline earth metal formates or other impurities which are formed in the inorganic Cannizzaro process. Likewise, the crude TMP contains only small amounts, from about 5 to 10 mol %, of trialkylammonium formates or free trialkylamine, unlike the product obtained from the organic Cannizzaro process.

The crude TMP which comes from the hydrogenation and is to be subjected to the purification process of the present invention comprises trimethylolpropane and water together with methanol, trialkylamine, trialkylammonium formate, longer-chain linear and branched alcohols and diols, for example methylbutanol or ethylpropanediol, addition products of formaldehyde and methanol onto trimethylolpropane, acetals such as dimethylolbutyraldehyde TMP acetal and di-TMP.

Good results are obtained using crude hydrogenation products comprising from 10 to 40% by weight of trimethylolpropane, from 0 to 10% by weight of 2,2-dimethylolbutanal, from 0.5 to 5% by weight of methanol, from 0 to 6% by weight of methylbutanol, from 1 to 10% by weight of trialkylammonium formate, from 0 to 5% by weight of 2-ethylpropanediol, from 0.1 to 10% by weight of high boilers such as di-TMP or other addition products and from 5 to 80% by weight of water. Crude hydrogenation products having such a composition can be obtained, for example, by the process described in WO 98/28253. Before the purification of the present invention to decompose the trialkylammonium formate-, the crude hydrogenation product can firstly be worked up by continuous distillation as described in examples 2 and 3 of DE-A-199 63 435. However, the purification according to the present invention of the crude hydrogenation products is preferably carried out without prior treatment by distillation.

Catalysts used in the process of the present invention are heterogeneous catalysts comprising at least one metal of groups 8 to 12 of the Periodic Table, for example ruthenium, osmium, iridium, platinum, palladium, rhodium, iron, copper, cobalt, nickel and zinc and also combinations of these metals. These metals can be used either in the form of the pure metals or in the form of their compounds, for example oxides or sulfides. Preference is given to using copper, nickel, cobalt, ruthenium or palladium catalysts. These catalysts can have been applied to the customary-supports, for example $TiO_2$, $Al_2O_3$, $ZrO_2$, $SiO_2$, carbon or mixtures thereof. The supported catalysts obtained in this way can also be in the form of all known shaped bodies. Examples are extrudates or pellets.

The use of supported copper-, nickel- and/or cobalt-containing catalysts is preferred.

Raney copper, Raney nickel and Raney cobalt catalysts are suitable for use in the process of the present invention. These Raney catalysts can be in the form of all known shaped bodies, for example pellets, extrudates or granules. Suitable Raney copper catalysts are, for example, the Raney copper catalysts in the form of nuggets which are known from WO 99/03801, which is hereby expressly incorporated by reference. These catalysts have a particle size of the nuggets of from 2 to 7 mm, a copper content of from 40 to 90% by weight, a surface area determined by the Langmuir method of from 5 to 50 $m^2/g$, a copper surface area of from 0.5 to 7 $m^2/g$, an Hg pore volume of from 0.01 to 0.12 ml/g and a mean pore diameter of from 50 to 300 nm.

EP-A-672 452, which is hereby expressly incorporated by reference, discloses suitable nickel-containing catalysts which comprise from 65 to 80% of nickel, calculated as nickel oxide, from 10 to 25% of silicon, calculated as silicon dioxide, from 2 to 10% by weight of zirconium, calculated as zirconium oxide, and from 0 to 10% by weight of aluminum, calculated as aluminum oxide, with the proviso that the sum of the contents of silicon dioxide and aluminum oxide is at least 15% (percentages quoted are by weight and are based on the total mass of the catalyst), and are obtainable by addition of an acidic aqueous solution of nickel, zirconium and, if desired, aluminum salts to a basic aqueous solution of silicon and, if desired, aluminum compounds, with the pH being reduced to at most 6.5 and subsequently being adjusted to from 7 to 8 by addition of further basic solution, isolation of the solid which has been precipitated this way, drying, shaping and calcination.

Furthermore, the hydrogenation catalysts known from EP-A-044 444, which is hereby expressly incorporated by reference, which have a specific surface area of from 50 to 150 $m^2/g$, which have, either entirely or partly, a spinel structure, in which copper is present in the form of copper oxide and in whose preparation copper and aluminum are precipitated from their compounds in a ratio of from 0.25 to 3 atoms of copper to one atom of aluminum in the presence of carbonates at a pH of from 4.5 to 9 and the precipitate obtained in this way is calcined at from 300 to 800° C.

The zirconium-, copper-, cobalt- and nickel-containing catalyst known from DE-A 198 26 396, which is free of oxygen-containing compounds of molybdenum, is also suitable for use in the process of the present invention.

In a particularly preferred embodiment, the purification according to the present invention is carried out in the presence of the catalyst known from DE-A 198 09 418, which is hereby expressly incorporated by reference, which comprises an inorganic support in which $TiO_2$ is present and, as active component, copper or a mixture of copper with at least one metal selected from the group consisting of zinc, aluminum, cerium, noble metals and metals of transition group VIII and whose specific copper surface area is not more than 10 $m^2/g$. These catalysts preferably have $TiO_2$ or a mixture of $TiO_2$ and $Al_2O_3$ or a mixture of $TiO_2$ and $ZrO_2$ or a mixture of $TiO_2$, $Al_2O_3$ and $ZrO_2$ as support; particular preference is given to using $TiO_2$. In the preparation of this catalyst as described in DE-A 19809418, metallic Cu powder can be added as further additive during tableting so that the copper surface area is not more than 10 $m^2/g$.

In a particular embodiment of the invention, the decomposition of the trialkylammonium formate present in the crude TMP is carried out over a catalyst suitable for the hydrogenation of the precursor of the TMP (2,2-dimethylolbutanal), for example over the copper catalyst known from DE-A-198 09 418.

This embodiment is particularly economical since the decomposition of the trialkylammonium formate can occur in the hydrogenation reactor of the hydrogenation process as described in WO 98/28253 and only one catalyst is required. The decomposition products of the trialkylammonium formate, viz. CO and water and/or $CO_2$ and hydrogen, can be removed from the reactor via the offgas line. However, the decomposition of the trialkylammonium formates according to the process of the present invention can likewise be carried out in a separate reactor.

In the process of the present invention, the decomposition of the trialkylammonium formates is generally carried out at from 100 to 250° C., preferably from 140 to 220° C. The pressures used are generally above $10^6$ Pa, preferably in the range from $2 \times 10^6$ to $15 \times 10^6$ Pa.

The process of the present invention can be carried out either continuously or batchwise, with preference being given to a continuous process.

In a continuous process, the amount of crude trimethylolalkane from the hydrogenation process or the organic Cannizzaro process is preferably from about 0.05 to about 3 kg per liter of catalyst per hour, more preferably from about 0.1 to about 1 kg per liter of catalyst per hour.

As hydrogenation gases, it is possible to use any gases which comprise free hydrogen and do not contain harmful amounts of catalyst poisons, for example CO. For example, it is possible to use offgases from a reformer. Preference is given to using pure hydrogen.

The process of the present invention is illustrated by the examples below.

EXAMPLES

Preparation of Crude TMP

An apparatus comprising two heatable stirred vessels connected to one another by means of overflow pipes and having a total capacity of 72 l was supplied with fresh aqueous formaldehyde solution (4 300 g/l in the form of a 40% strength aqueous solution) and n-butyraldehyde (1 800 g/h) and with fresh trimethylamine as catalyst (130 g/h) in the form of a 45% strength aqueous solution. The reactors were maintained at 40° C.

The output was fed directly into the upper part of a falling film evaporator with superposed column (11 bar steam for heating) and fractionally distilled there under atmospheric pressure to give a low-boiling top product consisting essentially of n-butyraldehyde, ethyl acrolein, formaldehyde, water and trimethylamine and a high-boiling bottom product.

The top product was condensed continuously and recirculated to the above-described reactors.

The high-boiling bottom product from the evaporator (about 33.5 kg/h) was admixed continuously with fresh trimethylamine catalyst (50 g/h, in the form of a 45% strength aqueous solution) and introduced into a heatable tube reactor which was provided with random packing and had an empty volume of 12.1. The reactor was maintained at 40° C.

The output from the after-reactor was introduced continuously into the upper part of a further distillation apparatus, viz. the formaldehyde removal (11 bar steam for heating), and fractionally distilled there to give a low-boiling top product consisting essentially of ethyl acrolein, formaldehyde, water and trimethylamine and a high-boiling bottom product. The low-boiling top product (27 kg/h) was condensed continuously and recirculated to the first stirred vessel, while the high-boiling bottom product was collected.

The bottom product obtained in this way consisted essentially of water together with dimethylol butyraldehyde, formaldehyde and traces of monomethylol butyraldehyde. It was then subjected to a continuous hydrogenation. For this purpose, the reaction solution was hydrogenated at 90 bar and 115° C. in a main reactor operated in the circulation/downflow mode and a downstream after-reactor operated in the circulation mode. The catalyst was prepared by a method analogous to catalyst J in DE 198 09 418. It comprises 40% of CuO, 20% of Cu and 40% of $TiO_2$. The apparatus used comprised a 10 m long heated main reactor (internal diameter: 27 mm) and a 5.3 m long heated after-reactor (internal diameter: 25 mm). The flow around the circuit was 25 l/h of liquid, and the feed to the reactor was set to 4 kg/h. Accordingly, 4 kg/h of hydrogenation product were taken off.

Examples 1 to 4

The TMP used has the composition 25% by weight of TMP, 0.35% by weight of 2,2-dimethylolbutanal, 0.53% by weight of methanol, 0.078% by weight of methylbutanol, 0.23% by weight of ethylpropanediol, 0.43% by weight of adducts of TMP with formaldehyde and methanol, 0.036% by weight of TMP formate, 0.46% by weight of TMP dimethylbutanal acetals, 0.46% by weight of high boilers, 1.7% by weight of trimethylammonium formate and 70% by weight of water. 180 ml of this crude solution were treated with hydrogen at 180° C. and 90 bar in the presence of a catalyst as indicated in table 1 which had been prereduced at 180° C. and 25 bar. After one hour, the dimethylolbutanal content and the TMP content were determined by gas chromatography. The formate concentration was determined by means of titration with tetrabutylammonium hydroxide. The results obtained are summarized in table 1.

Comparative Example 5

The procedure of examples 1 to 4 was repeated, but the reaction was carried out in the absence of a catalyst. The result is shown in the table.

| No. | Catalyst | Shaped bodies | Amount of catalyst [g] | DMB % by area[1] | TMP % by area[1] | Formate % by weight[2] | Formate conversion [%] |
|---|---|---|---|---|---|---|---|
| | Starting material | | | 1.17 | 83.4 | 0.74 | — |
| 1 | Cu/$TiO_2$ (DE 198 09 418) | 3 × 3 mm pellets | 20 | 0 | 85.1 | 0.33 | 55 |
| 2 | Cu/$Al_2O_3$ (EP 0 044 444) | 5 × 5 mm pellets | 9.5 | 0 | 85.2 | 0.40 | 46 |
| 3 | Ni/$SiO_2$/$Al_2O_3$/$ZrO_2$ (EP 0672 452) | 1.5 mm extrudates | 12.5 | 0 | 84.5 | 0.09 | 87 |
| 4 | Co/Ni/Cu/$ZrO_2$ (DE 198 26 396) | 5 × 3 mm pellets | 20.5 | 0 | 85.1 | 0.31 | 58 |
| 5 | — | — | — | 0 | 83.4 | 0.71 | 4 |

[1]GC analysis (detection without water)
[2]Titration with tetrabutylammonium hydroxide
[3]DMB = 2,2-dimethylbutanal It can be seen from the table that ammonium formate can be decomposed catalytically with high conversions at 180° C. over the above Cu, Ni and Co catalysts. On the other hand, virtually no formate conversion is achieved under purely thermal conditions in the comparative example. In addition, it is clear that the TMP yield is increased by hydrogenation of DMB under the conditions according to the present invention.

What is claimed is:

1. A process for removing trialkylammonium formate from a crude hydrogenation product comprising the trialkylammonium formate and a methylolalkane, which process comprises providing a crude hydrogenation product obtained in a hydrogenation process in which an alkanal and formaldehyde are reacted in the presence of a tertiary amine to form a dimethylolalkanal and the dimethylolalkanal is subsequently hydrogenated in a hydrogenation reactor to form the methylolalkane, and removing the trialkylammonium formate from the crude hydrogenation product by exposing the crude hydrogenation product, without prior treatment by distillation, to an elevated temperature, to a hydrogen-containing gas and to a catalyst comprising at least one metal of groups 8 to 12 of the Periodic Table.

2. The process defined in claim 1, wherein the catalyst is a supported copper-, nickel- and/or cobalt-containing catalyst.

3. The process defined in claim 1, wherein the catalyst is a catalyst capable of hydrogenating 2,2-dimethylolbutanal.

4. The process defined in claim 1, wherein the methylolalkane is trimethylolpropane.

5. The process defined in claim 1, wherein the trialkylammonium formate is removed at a temperature of from 100 to 250° C.

6. The process defined in claim 1, wherein the trialkylammonium formate is removed at a pressure of from $2 \times 10^6$ to $15 \times 10^6$ Pa.

7. The process defined in claim 1, which is carried out in the hydrogenation reactor employed in the hydrogenation process.

8. The process defined in claim 7, wherein the trialkylammonium formate is removed at a temperature of from 140 to 220° C.

9. The process defined in claim 1, wherein the trialkylammonium formate is removed at a temperature of from 140 to 220° C.

10. The process defined in claim 1, wherein the trialkylammonium formate is removed continuously.

11. The process defined in claim 10, wherein the crude hydrogenation product is employed in an amount of from about 0.05 to about 3 kg per liter of the catalyst per hour.

12. The process defined in claim 10, wherein the crude hydrogenation product is employed in an amount of from about 0.1 to about 1 kg per liter of the catalyst per hour.

* * * * *